United States Patent [19]

Kogo et al.

[11] Patent Number: 4,891,575
[45] Date of Patent: Jan. 2, 1990

[54] PARTICLE DETECTOR USING INLET AND OUTLET PIPES AS ELECTRODES

[75] Inventors: Katsuyuki Kogo; Shinji Miyasaka, both of Osaka, Japan

[73] Assignee: Sumitomo Electric Industries, Ltd., Osaka, Japan

[21] Appl. No.: 376,152

[22] Filed: Jul. 6, 1989

Related U.S. Application Data

[63] Continuation of Ser. No. 180,619, Apr. 4, 1988, abandoned, which is a continuation of Ser. No. 815,645, Jan. 2, 1986, abandoned.

[30] Foreign Application Priority Data

Jan. 8, 1985 [JP] Japan .................................. 60-1931

[51] Int. Cl.⁴ ............................................. G01N 27/07
[52] U.S. Cl. .................................. 324/71.4; 324/71.1; 324/446
[58] Field of Search ...................... 324/71.4, 71.1, 450, 324/446, 454; 377/11, 12; 204/1 T, 417, 420

[56] References Cited

U.S. PATENT DOCUMENTS

| | | | |
|---|---|---|---|
| 3,281,348 | 10/1966 | Schumacher et al. | 324/446 X |
| 3,779,279 | 12/1973 | Schön | 324/71.1 X |
| 3,783,376 | 1/1974 | Doniguian | 324/71.1 |
| 3,855,098 | 12/1974 | Fletcher | 204/420 |
| 3,868,498 | 2/1975 | Guggenbuhl | 235/151.3 |
| 3,958,177 | 5/1976 | Reeves et al. | 324/71.1 |
| 4,157,499 | 6/1979 | Kacerek | 377/12 |
| 4,180,091 | 12/1979 | Hanley et al. | 324/71.4 X |
| 4,484,134 | 11/1984 | Halloran | 324/71.1 |
| 4,594,553 | 6/1986 | Varga | 324/454 |

FOREIGN PATENT DOCUMENTS 2812470 3/1979 Fed. Rep. of Germany .
2855371 3/1980 Fed. Rep. of Germany .

Primary Examiner—Reinhard J. Eisenzopf
Assistant Examiner—Jack B. Harvey
Attorney, Agent, or Firm—Cushman, Darby & Cushman

[57] ABSTRACT

A particle detector in which a pair of pipe elements are coupled together through an aperture and the liquid to be tested is passed through the pipe elements and the aperture with a voltage or current applied to the liquid through the pipe elements acting as electrodes so that the diameter of the pipe elements is reduced because the electrodes are not provided in the pipe elements.

8 Claims, 4 Drawing Sheets

PARTICLE DETECTOR USING INLET AND OUTLET PIPES AS ELECTRODES

This is a continuation of application Ser. No. 07/180,619, filed Apr. 4, 1988, which was a continuation of application Ser. No. 06/815,645 filed Jan. 2, 1986 abandoned.

BACKGROUND OF THE INVENTION

1. Field Of The Invention

The present invention relates to a particle detector for use in the detection and measurement of a number of fine particle such as blood cells.

2. Description Of The Prior Art

There are known two kinds of methods of detecting and counting the number of fine particle such as cells, an optical system using laser light and an electronic method using electric conductivity measurement. The latter system is superior to the former system partly because the whole measurement system is inexpensive and partly because the volume of the object of the measurement can be reflected in the result of the measurement.

A blood cell counter is a typical particle counter using the electric conductivity measurement. A summary of the particle counter of the electric conductivity type will be explained hereinafter.

The particle counter of this type comprises two liquid tanks coupled together through a fine aperture and a pair of electrodes connected to the liquid in the liquid tanks. In measurement, the current of the pair of electrodes is measured applying suitable constant DC current or the voltage across the pair of electrodes is measured applying suitable constant DC current to the electrodes while the liquid flows from the first tank to the second tank through the aperture. In this arrangement, the impedance between the pair of electrodes changes every time the particles such as cells pass through the aperture since the impedance depends on the particles present in the interior of and near the aperture, so that the voltage or current measured across the electrodes is changed in a pulsed manner. Therefore, by counting the number of the pulses or by measuring the amplitude of the pulse, the number of or the size of the particles can be measured.

Although the method mentioned above is suitable for measuring the number and density of the particles, it is impossible to isolate every particle and to divide the particles since the particles are discharged external of the tank through a long discharge tube acting as the part of the great capacity tank after the aperture.

SUMMARY OF THE INVENTION

An essential object of the present invention is to provide a particle detector which is able to isolate and/or divide the particles easily.

Another object of the present invention is to provide a particle detector which is able to reduce the diameter of the pipes through which the liquid flows so that the control of the flow of liquid is easy.

A further object of the present invention is to provide a particle detector which is effective to prevent corrosion of the pipes, thereby enabling correct particle measurement.

According to the present invention, there is provided a particle detector which comprises a pair of pipe means for feeding liquid to be tested, means for coupling said pipe means through an aperture provided in the coupling means to communicate the liquid from one of the pipe means to another pipe means, means for applying voltage or current to the liquid present both sides of said aperture, said applying means being disposed on the pipe means or outside of the pipe means, and means for detecting change of the voltage or current occurring across the liquid present in both sides of the aperture.

In the arrangement mentioned above, the applying means which are the electrodes to apply voltage or current to the liquid containing particles are not placed inside the pipe means, so that the diameter of the pipe means can be reduced, thereby enabling isolation of the particles easy.

DETAILED DESCRIPTION OF THE PREFERRED EMBODIMENTS

Figure 1:
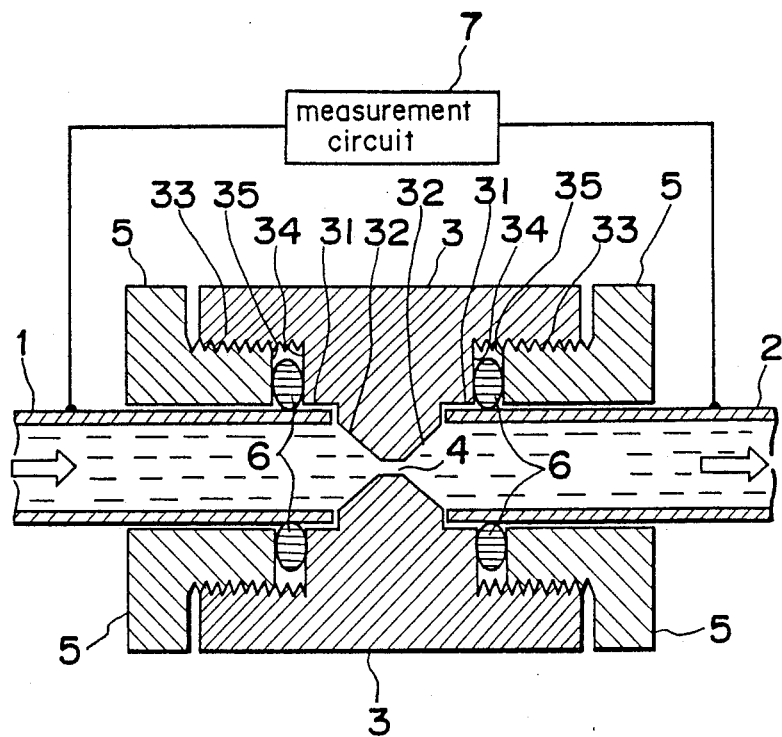
FIG. 1 is a cross sectional view showing on example of a particle detector according to the present invention.

A pair of pipes 1 and 2 made of electrical conductive material such as stainless steel are coupled together through a coupling unit 3 made of electrical insulating material. Both of the pipes 1 and 2 are detachably inserted in ports 31 having relatively large diameters. The ports 31 taper in to an aperture 4 through tapered portions 32 and the pipes 1 and 2 are communicated together through the aperture 4. The end portions of the pipes 1 and 2 are passed through connecting screws 5 which are engaged and screwed in connecting holes 33 respectively so that when the connecting screws 5 are fastened, each of sealing rings 6 fitted to the pipes 1 and 2 are clamped between the stepped face 34 of the coupling unit 3 and the end face 35 of the fasting screw 5, whereby the pipes 1 and 2 can be detachably fastened to the coupling unit 3 while hydraulically sealed. A particle measurement circuit 7 is connected to the pipes 1 and 2 to apply a DC constant voltage or DC current to the pipes 1 and 2 acting as the electrodes so that the size and number of the particles passing through the aperture 4 can be detected by the operation hereinafter described.

When measuring the particles, the liquid to be measured is supplied to the pipe 1. The liquid containing particles thus applied to the pipe 1 flows to the pipe 2. The particle measuring circuit 7 detects the change of the voltage or current across the pipes 1 and 2 every time the particles pass the aperture 4 one by one. In the embodiment shown in FIG. 1, only one particle can pass the aperture 4 by reducing the diameter of the aperture 4 up to near the particle size.

Since the pipes 1 and 2 act as electrodes, there is no need to provide any discrete electrodes in the device. The absence of the electrode inside the pipe enables to suppress occurrence of turbulence of flow of the liquid in the pipes 1 and 2. Also the absence of the electrode inside the pipes 1 and 2 enables to reduce the diameter of the pipe i.e., pipes of small diameter can be used whereby the quantity of the liquid flowing in the pipes 1 and 2 can be easily defined, therefore, the isolation and/or division of the liquid can be easily and correctly controlled. Also, since the pipes 1 and 2 are coupled directly to the aperture in a body, the device can be made compact.

It is noted that the pipes 1 and 2 may be formed in such a manner that only the parts of the pipes near the aperture 4 are made of electrical conductive materials and the other parts of the pipes are made of insulation materials. Also, the pipes per se may be made insulation materials with the inner cylindrical surface of the pipes coated with an electrical conductive layer.

In case the polarity of the pipes acting as the electrodes is unchanged, there may occur polarization on the electrodes, resulting in voltage drop near the electrodes, whereby the voltage applied to the liquid across the both sides of the aperture 4 may be reduced, and the correct measurement of the particles may be harmed.

In order to avoid such difficulty mentioned above, the pipes 1 and 2 may be made of silver with the inner cylindrical surface thereof formed of silver chloride and the liquid contains chloride ion so that oxidation and reduction occur reversibly under substantially same potential in the silver/silver chloride electrodes, thereby enabling to prevent the polarization.

Figure 2:
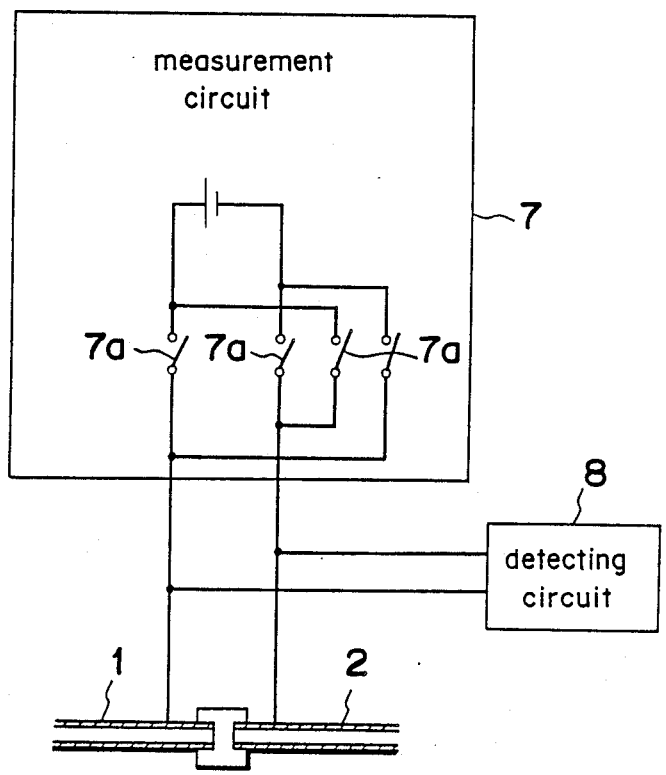
FIG. 2 is a block diagram showing an example of a circuit used in the particle detector shown in FIG. 1.
Figure 3:
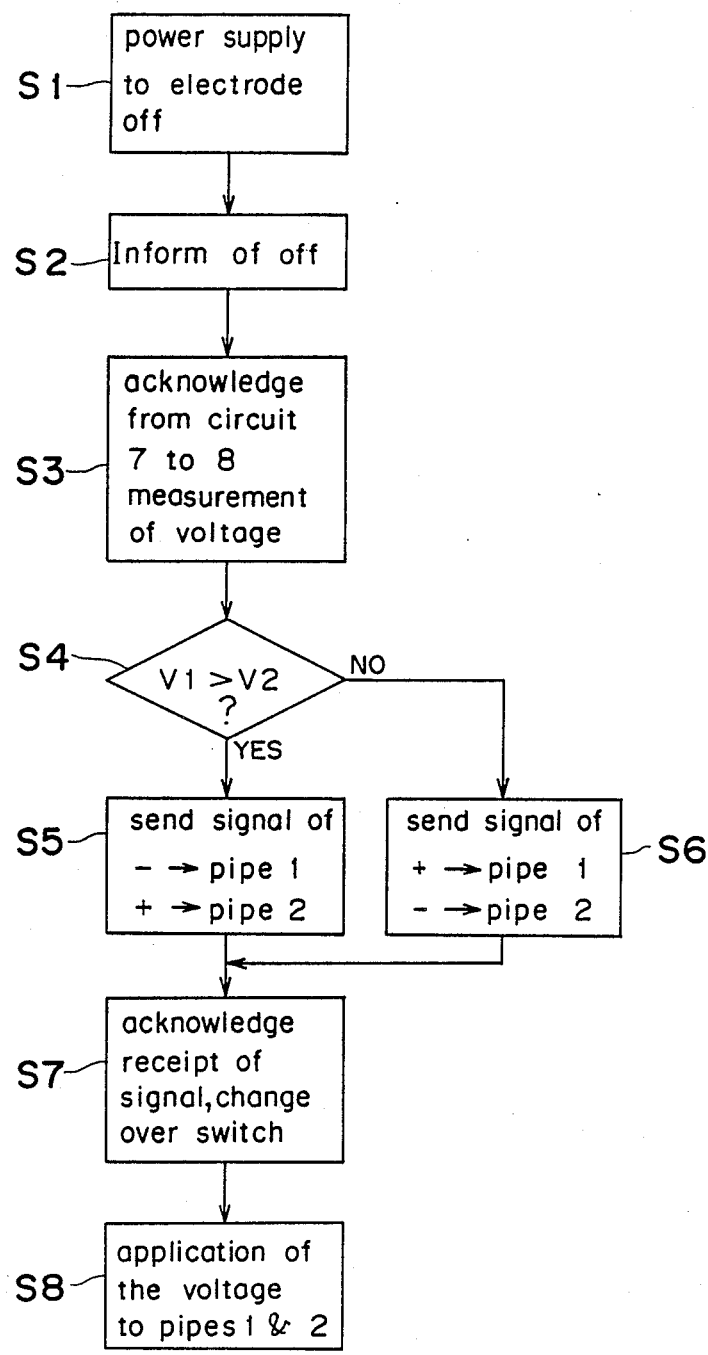
FIG. 3 is a flow chart showing an operation of the device shown in FIG. 2.

Referring to FIG. 2 showing a modification of the particle detecting device according to the present invention in which there is provided a detecting circuit 8 for detecting the voltage applied to the pipes 1 and 2. The detecting circuit 8 outputs a control signal to change over the polarity of the pipes 1 and 2 in response to the voltage across the pipes 1 and 2. In order to change over the polarity of the pipes 1 and 2, a switch circuit 7a is provided in the measurement circuit 7. The operation of the arrangement shown in FIG. 2 is explained hereinafter with reference to the flow chart of FIG. 3.

In the step S 1, the application of the power to the pipes 1 and 2 is turned off. The off state of the power is informed from the measurement circuit 7 to the detection circuit 8 in the step S 2. Upon reception of the off state, the detecting circuit 8 sends the reception of the off state of the power to the measurement circuit 7 in the step S 3 and effects to measure the voltage across the pipes 1 and 2. It is detected in the step S 4 whether the potential V1 of the pipe 1 is higher than the potential V2 of the pipe 2. In case the potential V1 of the pipe 1 is higher than the potential V2 of the pipe 2, the program flow goes to the step S 5, wherein the detecting circuit 8 outputs the control signal to make the pipe 1 negative polarity and the pipe 2 positive polarity to the measurement circuit 7. In case the potential V2 of the pipe 2 is higher than the potential V1 of the pipe 1, the program flow goes to the step S 6, wherein the detecting circuit 8 outputs the control signals to make the pipe 1 positive polarity and the pipe 2 negative polarity. The program flow goes to the step S 7, wherein the measurement circuit 7 controls the switch circuit 7a to supply the power to the pipes 1 and 2 as defined by the control signal obtained in any one of the steps S 5 and S 6 so as to change over the polarity applied to the pipes 1 and 2. Also the measurement circuit 7 sends the acknowledge of reception of the control signal to the detecting circuit 8. Then the measurement circuit 7 applies the power to the pipes 1 and 2. Changing over the polarity of the pipes 1 and 2 as mentioned above enables to prevent consumption of the silver chloride at only one side of the pipes 1 or 2.

Figure 4:
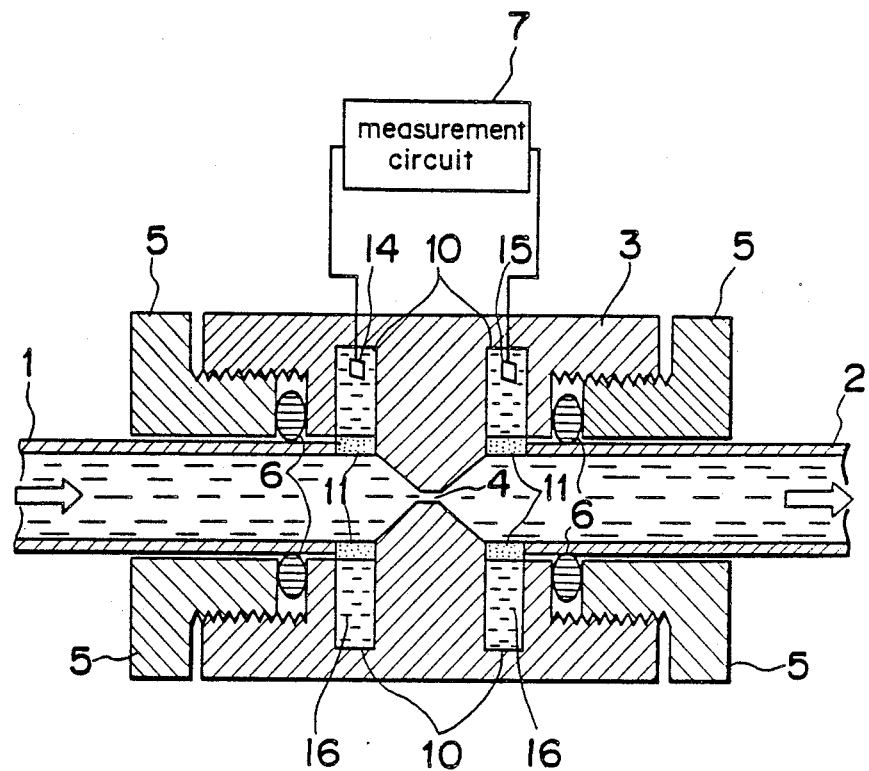
FIG. 4 is a cross sectional view showing another embodiment of the particle detector according to the present invention.

Referring to FIG. 4 showing another modification of the particle detecting device according to the present invention in which air bubbles occurring at the pipes 1 and 2 or electrodes can be collected to prevent the air bubbles from entering in the liquid.

A pair of cavities 10 are formed on both outer portions of the aperture 4 in the coupling unit 3, in a cylindrical shape coaxial with the aperture 4. A pair of partition rings 11 made of porous material are respectively disposed in the cavities 10 aligned with the pipes 1 and 2 so as to separate the path of the liquid flowing the pipes 1 and 2 and the aperture 4 from electrolyte 16 contained in the cavities 10. A pair of electrodes 14 and 15 are soaked in the electrolyte 16 and the electrodes 14 and 15 are connected with the measurement circuit 7 to receive the DC voltage or current. In this embodiment, the pipes 1 and 2 may be made of electrical insulating material with a suitable corrosion resistance materials such as plastic resin. The partition rings 11 may be made of tight ceramic, bore glass or bore filter having holes of 50 to 1000 A diameter so as to prevent to pass the particles but the electrical conduction by the ions can be obtained.

By this arrangement, since the air bubbles occurring in the cavities 10 near the electrodes 14 and 15 stays in the cavities 10 preventing entering of the bubbles into the aperture keeping the electrical conduction so that the particle measurement can be performed.

In this embodiment, the particle measurement can be performed by counting the number of pulses of the current or voltage occurring on the electrodes 14 and 15 in a similar manner as performed in the embodiments already described.

In one example, the internal diameter of the pipes 1 and 2 is 0.5 to 1 mm. The diameter of the aperture 4 may be 100 μm.

It is an advantage of the particle detector according to the present invention that since the diameter of the pipes and the aperture can be made small, the flow of the particles can be easily controlled, whereby the isolation and/or the division of the liquid may be made easily.

What is claimed is:

1. A particle detector which comprises:
first and second pipe means for feeding liquid to be treated;
means for coupling said first and second pipe means to one another, said coupling means being an elongated cylindrical shape having two end portions in an axial direction that define two threaded holes, defining an aperture to communicate liquid from one of the pipe means to the other pipe means with a diameter to pass only one particle at a time and being tapered between said aperture and each of said end portions;
means for applying voltage or current to the liquid present in both sides of said aperture;
at least one connecting screw which is detachably and threadingly engaged with each threaded hole of said coupling means and has a through hole to receive and pass said pipe means;
means for detecting change of the voltage or current occurring across the liquid present in both sides of the aperture, whereby particles passing through the aperture may be detected; and
an O-ring disposed in a space between said coupling means and said connecting screw so that said O-ring is clamped between an end face of said connecting screw and an end face of said coupling means and is deformed when said connecting screw completely engages said coupling means to further secure said pipe means.

2. The particle detector according to claim 1, wherein said applying means comprises an electrically conductive member on said pipe means.

3. The particle detector according to claim 1, wherein said pipe means are made of metal.

4. The particle detector according to claim 1, wherein said pipe means are principally made of electrical insulating material, and wherein the portions of the pipe means near the aperture are made of electrically conductive materials.

5. The particle detector according to claim 1, wherein said pipe means are made principally of electrical insulating materials, and wherein the inner surface of said pipe means is coated with electrically conductive materials.

6. The particle detector according to claim 1, wherein said pipe means are principally made of silver with the inner surface of the pipe means covered by silver chloride, and wherein the liquid contains chloride ions.

7. The particle detector according to claim 1, wherein said detecting means further comprises means for changing over the polarity of the current or voltage applied to said pipe means corresponding to the voltage difference across the two pipes.

8. The particle detector according to claim 1, wherein said applying means comprises a pair of cavities formed in the coupling means with an electrolyte contained in the cavities;

electrodes disposed in the cavities; and partition rings for separating the liquid flowing through the aperture and the electrolyte, said partition ring being made of ion conductive and porous materials.

* * * * *